United States Patent [19]

Loev et al.

[11] Patent Number: 4,614,747
[45] Date of Patent: Sep. 30, 1986

[54] DERIVATIVES OF ALPHA-ALKYL POLYOLEFINIC CARBOXYLIC ACID USEFUL IN THE TREATMENT OF PSORIASIS

[75] Inventors: Bernard Loev, Scarsdale; Howard Jones, Ossining; Wan-kit Chan, Yorktown Heights, all of N.Y.

[73] Assignee: USV Pharmaceutical Corp., Tuckahoe, N.Y.

[21] Appl. No.: 676,352

[22] Filed: Nov. 29, 1984

Related U.S. Application Data

[62] Division of Ser. No. 518,785, Jul. 29, 1983, Pat. No. 4,523,042.

[51] Int. Cl.$^4$ .................. C07C 43/15; C07C 43/21; C07C 43/215; C07C 43/188
[52] U.S. Cl. ........................ 514/529; 568/328; 568/329; 568/376; 568/377; 568/378; 568/579; 568/631; 568/632; 568/633; 568/646; 568/654; 568/659; 568/660; 568/667; 568/668; 568/670; 560/128; 514/682; 514/683; 514/690; 514/715; 514/717; 514/719; 514/722; 514/723
[58] Field of Search ............... 568/668, 654, 646, 631, 568/378, 667, 632, 670, 376, 377, 579, 633, 659, 660, 329, 328; 560/128; 514/529, 682, 683, 690, 715, 717, 719, 722, 723

[56] References Cited

U.S. PATENT DOCUMENTS

| | | | |
|---|---|---|---|
| 2,451,738 | 10/1948 | Isler | 568/668 |
| 2,941,009 | 6/1960 | Weisler | 568/668 |
| 4,147,708 | 4/1979 | Manchand | 568/654 X |
| 4,224,244 | 9/1980 | Bollag et al. | 568/631 X |

*Primary Examiner*—Bernard Helfin

[57] ABSTRACT

This invention relates to novel compounds having pharmaceutical activity and having the general structure

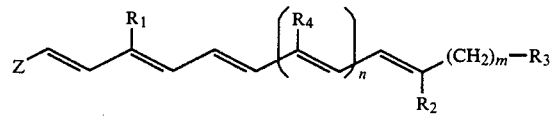

wherein the Z, $R_1$, $R_2$, $R_3$, $R_4$, n and m are defined within.

5 Claims, No Drawings

DERIVATIVES OF ALPHA-ALKYL POLYOLEFINIC CARBOXYLIC ACID USEFUL IN THE TREATMENT OF PSORIASIS

This application is a division of copending application Ser. No. 518,785, filed July 29, 1983, and now U.S. Pat. No. 4,523,042.

BACKGROUND OF THE INVENTION

The present invention relates to novel alpha-alkyl polyolefinic carboxylic acids derived from such polyolefinic intermediates as retinal(3,7-dimethyl-9-(2,6,6-trimethyl-1-cyclohexen-1-yl)-2,4,6,8-nonatetraenal; vitamin A aldehyde) which possesses the structure

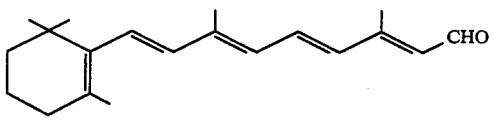

A synthesis of retinal from beta-ionone and propargyl halide is described in U.S. Pat. No. 3,060,229.

A number of alpha-substituted polyolefinic carboxylic acids, aldehydes, and esters are described in the scientific literature. Japanese Pat. No. 10,124 (1964), C.A. 62, 2798 g (1965) describes 2,7-dimethyl-9-(2,6,6-trimethyl-1-cyclohexen-1-yl)-2,4,6,8-nonatetraenoic acid and 2,7,11-trimethyl-13-(2,6,6-trimethyl-1-cyclohexen-1-yl)-2,4,6,8,10-12-tridecahexanenoic acid; Machleidt, et al., *Justus Liebigs Ann. Chem.*, 679,20 (1964) describes α-fluoropolyolefinic acids and esters; Chan, et al., *J.A.C.S.* 96, 3642 (1974) describe polyolefinic carboxaldehydes; Haeck, et al., *Recuil* 85 (1966) pp. 334–338 describe 5,9-dimethyl-11-(2,6,6-trimethyl-1-cyclohexen-1-yl)-2,4,6,8,10-undecapentaenoic acid and corresponding 2,4,6,8,10-12-tridecahexanenoic acids as well as the corresponding α-cyano and α-carboxy substituted compounds. Buchta, et al., *Naturwissenschaften* 46, 74 (1959) describe methyl-2-methyl-7-phenyl-2,4,6-heptatrienoate.

SUMMARY OF THE INVENTION

The present invention is directed to novel alpha-alkyl, polyolefinic compounds and derivatives thereof of the general formula

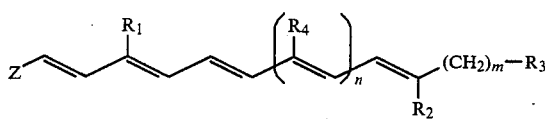

wherein
n is 0 to 3,
m is 0 to 1, and
$R_1$ and $R_4$ are each independently hydrogen or an alkyl group of from 1 to 5 carbon atoms;
$R_2$ is an alkyl group of from 1 to 5 carbon atoms;
$R_3$ is H, $C_1$–$C_5$ alkyl, cyclo $C_3$–$C_7$ alkyl, $C_2$–$C_5$ alkenyl, cyclo $C_3$–$C_7$ alkenyl, aryl, hydroxy, $C_1$–$C_5$ alkoxy, aryloxy, arylalkoxy, formyl, $C_1$–$C_6$ alkylcarbonyl, $C_2$–$C_5$ alkenylcarbonyl, arylcarbonyl, aryl $C_1$–$C_5$ alkylcarbonyl, aryl $C_2$–$C_5$ alkenylcarbonyl, $NR_5R_5$, $SR_5$,

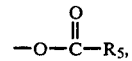

retinyloxy, retinoyl, retinoyloxy, or

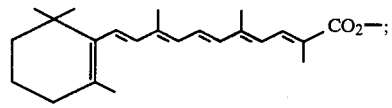

$R_5$ is independently H, $C_1$–$C_{20}$ alkyl, aryl, aralkyl, and
Z is a cycloalkyl, cycloalkenyl or cyclodialkenyl group substituted with from 0 to 5 alkyl groups, a keto group or a hydroxyl group, or a phenyl group substituted with from 0 to 4 hydroxy, alkoxy, alkyl or trifluoromethyl groups or halogen atoms or combinations thereof; and the pharmaceutically-acceptable salts thereof. The invention includes compounds wherein the double bonds are in the cis or trans configuration.

The foregoing compounds are effective in the treatment of psoriasis, acne, and cellular and humoral immunodeficiency.

DESCRIPTION OF THE PREFERRED EMBODIMENTS

A preferred group of compounds within the aforesaid general formula are those in which $R_1$ $R_2$ and $R_4$ are methyl, and Z is a cycloalkenyl group substituted with from 0 to 3 alkyl groups, or a phenyl group substituted with from 1 to 4 alkoxy or alkyl groups containing up to 5 carbon atoms or combinations of the foregoing, including those compounds in which one or more of the double bonds are in the cis configuration. Within this preferred group of compounds, still more preferred are compounds in which Z is the group 2,6,6-trimethyl-1-cyclohexen-1-yl. It is preferred also that n be 1.

The compounds of this invention can be prepared from known polyolefinic materials, e.g., retinal, employing known synthetic procedures of analogous polyolefinic compounds which can be prepared in accordance with methods known by those skilled in the art.

The compounds of the present invention are obtained by the following reaction scheme:

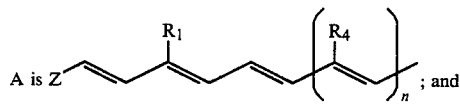

; and

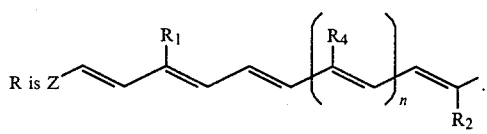

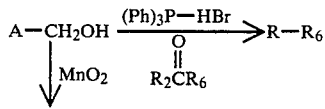

-continued

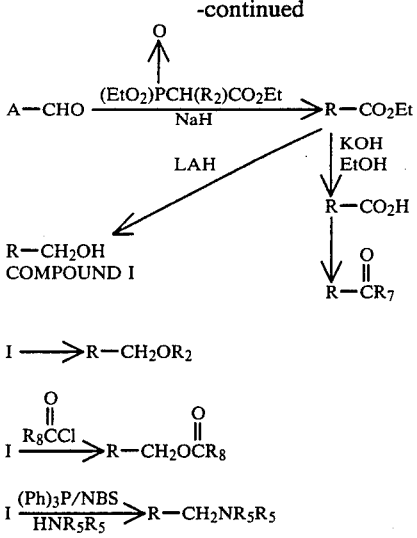

I ⟶ R—CH₂OR₂

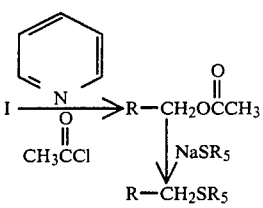

I $\xrightarrow{\text{(Ph)}_3\text{P/NBS}}_{\text{HNR}_5\text{R}_5}$ R—CH₂NR₅R₅

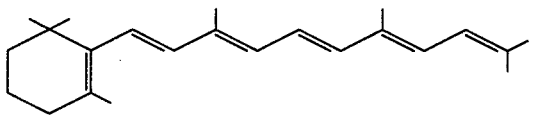

wherein
$R_6$ is H, $C_1-C_5$ alkyl, cyclo $C_3-C_7$ alkyl, $C_2-C_5$ alkenyl, cyclo $C_3-C_7$ alkenyl or aryl;
$R_7$ is $R_6$, aryl $C_1-C_5$ alkyl, aryl $C_2-C_5$ alkenyl or retinyl;
$R_8$ is $R_5$, aryl, retinyl, or

[structure of retinyl group]

Z, $R_1$, $R_2$, $R_4$ and $R_5$ are as described above.

EXAMPLE 1

2,5,9-Trimethyl-11-(2,6,6-trimethyl-1-cyclohexen-1-yl)-2,4,6,8,10-undecapentaene Retinol (2 g, 7 mmol) is dissolved in 50 ml of toluene and 2.4 g (7 mmol) of triphenylphosphonium hydrobromide is added. The mixture is stirred for 18 hours at room temperature and 2 hours at 60° C., then cooled and the toluene separated. The viscous sediment is digested four times with 25 ml of dry toluene. The final sediment is dissolved in 100 ml of methylene chloride. The solution is evaporated under reduced pressure and dried in vacuo to give retinyl triphenyl phosphonium bromide. This substance is dissolved in 40 ml of DMF and the resulting solution is cooled to −10° C. and 0.3 g of NaH, (50% dispersion in oil) is added carefully. The mixture is stirred for 2 hours and 4 g (0.07 mol) of acetone is added dropwise. After two hours at −10° C., the reaction mixture is stirred at room temperature for 18 hours and poured into 600 ml of ice-H₂O mixture. The mixture is extracted several times with hexane. The combined organic layers are washed with a mixture of methanol-H₂O (3:2, v/v) and brine, dried (Na₂SO₄), and evaporation of solvent under reduced pressure affords the crude product. Purification of the crude product with a dry column (hexane:petroleum ether, 1:1) gives 2,5,9-trimethyl-11-(2,6,6-trimethyl-1-cyclohexen-1-yl)-2,4,6,8,10-undecapentaene.

EXAMPLE 2

2,5,9-Trimethyl-11-(2,6,6-trimethyl-1-cyclohexen-1-yl)-2,4,6,8,10-undecapentaene-1-ol A solution of 2,5,9-trimethyl-11-(2,6,6-trimethyl-1-cyclohexen-1-yl)-2,4,6,8,10-undecapentaenoic acid ethyl ester (1.85 g, 5 mmol) in 25 ml of anhydrous THF is cooled to −10° C. and 0.19 g (5 mmol) of LAH is added in portions. The resulting mixture is stirred for 4 hours and quenched carefully with 0.4 ml of water. The mixture is suction-filtered and the residue thoroughly washed with ether. The combined filtrate and washings are dried (MgSO₄) and evaporated under reduced pressure to give the crude product. Purification by HPLC (4% ethylacetate in hexane on silica gel column) gives the pure desired product.

EXAMPLE 3

2,5,9-Trimethyl-11-(2,6,6-trimethyl-1-cyclohexen-1-yl)-2,4,6,8,10-undecapentaenyl acetate A solution of 2,5,9-trimethyl-11-(2,6,6-trimethyl-1-cyclohexen-1-yl)-2,4,6,8,10-undecapentaene-1-ol (1.6 g, 5 mmol) and pyridine (9.6 ml, 7.3 mmol) in 15 ml of anhydrous methylene chloride is stirred in an ice bath and a solution of acetyl chloride (0.37 ml, 5.25 mmol) in 5 ml of anhydrous methylene chloride is added dropwise. The mixture is stirred at 0° C. for 1½ hours and at room temperature for 30 minutes and then taken up in 250 ml of ether. The solution is washed with ice cold 5% aqueous sodium bicarbonate and water, dried (MgSO₄) and evaporated to give the crude product; recrystallization from ethanol affords the titled compound.

EXAMPLE 4

1-Phenylmercapto-2,5,9-trimethyl-11-(2,6,6-trimethyl-1-cyclohexen-1-yl)-2,4,6,8,10-undecapentaene To a solution of 1.85 g (5 mmol) of 2,5,9-trimethyl-11-(2,6,6-trimethyl-1-cyclohexen-1-yl)-2,4,6,8,10-undecapentaenyl acetate in 25 ml of anhydrous THF and 8 ml of HMPA is added in portions 0.68 g (5.2 mmol) of sodium thiophenoxide. The resulting mixture is stirred at room temperature for 18 hours and then taken up in 250 ml of diethyl ether. The solution is washed with saturated aqueous NH₄Cl and water, dried and evaporated in vacuo to give an oil. Purification on a silica gel dry column gives the desired product.

EXAMPLE 5

1-Methylamino-2,5,9-trimethyl-11-(2,6,6-trimethyl-1-cyclohexen-1-yl)-2,4,6,8,10-undecapentaene A solution of 2,5,9-trimethyl-11-(2,6,6-trimethyl-1-cyclohexen-1-yl)-2,4,6,8,10-undecapentaene-1-ol (3.2 g, 10 mmol) and triphenylphosphine (2.88 g, 11 mmol) in 20 ml of THF is stirred in an ice bath and 1.78 g (10 mmol) of N-bromosuccinimide is added in small portions over a period of one hour. After addition, the cooling bath is removed and the temperature of the reaction mixture is allowed to rise slowly to room temperature. The mixture is concentrated in vacuo and then diluted with a mixture of ether/petroleum ether. After sitting in refrigerator for several hours, white crystals of triphenylphosphine oxide occur, which is collected by filtration. The filtrate is concentrated and dissolved in 10 ml of dry DMF. To this solution is added 2 g of triethylamine and 0.68 g of methylamine hydrochloride. The resulting mixture is stirred at room temperature for 18 hours and poured into 500 ml of ice-water. The crude product is extracted into ethylacetate and washed with water. After drying over magnesium sulfate, the solvent is removed in vacuo to give the crude product as an oil. This substance is purified on HPLC (2% ethyl acetate in hexane, silica gel column) to give 1-methylamino-2,5,9-trimethyl-11-(2,6,6-trimethyl-1-cyclohexen-1-yl)-2,4,6,8,10-undecapentaene.

EXAMPLE 6

1-Methoxy-2,5,9-trimethyl-11-(2,6,6-trimethyl-1-cyclohexen-1-yl)-2,4,6,8,10-undecapentaene To a solution of 2,5,9-trimethyl-11-(2,6,6-trimethyl-1-cyclohexen-1-yl)-2,4,6,8,10-undecapentaene-1-ol (1.6 g, 5 mmol), 1.06 g (10 mmol) of trimethyl orthoformate and 160 mg (5 mmol) of dry methanol in 5 ml of dry THF is added dropwise a solution of 40 μL of trifluoroacetic acid in 1 ml of dry THF over a 1 minute period at room temperature. After overnight standing, the reaction mixture is poured into cold aqueous 5% NaHCO$_3$ and extracted with chloroform three times. The combined organic extract is washed with water, dried over Na$_2$SO$_4$ and evaporated in vacuo to give a residue, which is purified by HPLC (4% ether in hexane, silica gel column) to afford of 1-methoxy-2,5,9-trimethyl-11-(2,6,6-trimethyl-1-cyclohexen-1-yl)-2,4,6,8,10-undecapentaene as an oil.

EXAMPLE 7

3,6,10-Trimethyl-12-(2,6,6-trimethyl-1-cyclohexen-1-yl)-3,5,7,9,11-dodecapentaen-2-one A solution of 2,5,9-trimethyl-11-(2,6,6-trimethyl-1-cyclohexan-1-yl)-2,4,6,8,10-undecapentaenoic acid (3.4 g, 10 mmol) in 100 ml of anhydrous ether is stirred under an inert atmosphere in an ice bath and 20 mmol of methyllithium (11 ml of a 1.8M solution in diethyl ether) is added dropwise. The resulting mixture is stirred at room temperature for 1 hour and treated with 10 ml of ice cold water. The organic layer is separated and dried over MgSO$_4$. Removal of solvent in vacuo affords a residue which is purified by a dry column (hexane-ethylacetate, 2:1,) to give 3,6,10-trimethyl-12-(2,6,6-trimethyl-1-cyclohexen-1-yl)-3,5,7,9,11-dodecapentaen-2-one.

The following compounds can be prepared by procedures described in the above examples.

2,5,9-Trimethyl-11-(2,6,6-trimethyl-1-cyclohexen-1-yl)-2,4,6,8,10-undecapentaenyl palmitate;
2,5,9-Trimethyl-11-(2,6,6-trimethyl-1-cyclohexen-1-yl)-2,4,6,8,10-undecapentaenyl retinoate;
2,5,9-Trimethyl-11-(2,6,6-trimethyl-1-cyclohexen-1-yl)-2,4,6,8,10-undecapentaenyl 2,5,9-trimethyl-11-(2,6,6-trimethyl-1-cyclohexen-1-yl)-2,4,6,8,10-undecapentaenoate;
1-Retinyloxy-2,5,9-trimethyl-11-(2,6,6-trimethyl-1-cyclohexen-1-yl)-2,4,6,8,10-undecapentaene;
2,7-Dimethyl-9-(4-methoxy-2,3,6-trimethylphenyl)-2,4,6,8,nonatetraenyl palmitate;
11-(4-Methoxy-2,3,6-trimethylphenyl)-2,5,9-trimethyl-2,4,6,8,10-undecapentaene-1-ol;
2,7-Dimethyl-9-(2,6,6-trimethyl-1-cyclohexen-1-yl)-2,4,6,8-nonatetraene-1-ol;
11-(4-Methoxy-2,3,6-trimethylphenyl)-2,5,9-trimethyl-2,4,6,8,10-undecapentaenyl acetate;
2,5,9-Trimethyl-11-(2,6,6-trimethyl-2-cyclohexen-1-yl)-2,4,6,8,10-undecapentaene-1-ol;
2,5,9-Trimethyl-11-(2,6,6-trimethyl-1,3-cyclohexadien-1-yl)-2,4,6,8,10-undecapentaene-1-ol.

The therapeutic agents of this invention may be administered alone or in combination with pharmaceutically acceptable carriers, the proportion of which is determined by the solubility and chemical nature of the compound, chosen route of administration and standard pharmaceutical practice. For example, they may be administered orally in the form of tablets or capsules containing such excipients as starch, milk, sugar, certain types of clay and so forth. They may be administered orally in the form of solutions which may contain coloring and flavoring agents or they may be injected parenterally, that is, intramuscularly, intravenously or subcutaneously. For parenteral administration, they may be used in the form of a sterile solution containing other solutes, for example, enough saline or glucose to make the solution isotonic. When applied topically, the present new products can be provided in the form of dusting powders, aerosol sprays, ointments, aqueous compositions including solutions and suspensions, cream lotions and the like. In this regard, any of the commonly employed extending agents can be used depending on the nature of the product as is well-known in the art.

The physician will determine the dosage of the present therapeutic agents which will be most suitable and it will vary with the form of administration and the particular compound chosen, and furthermore, it will vary with the particular patient under treatment. He will generally wish to initiate treatment with small dosages substantially less than the optimum dose of the compound and increase the dosage by small increments until the optimum effect under the circumstances is reached. It will generally be found that when the composition is administered orally, larger quantities of the active agent will be required to produce the same effect as a smaller quantity given parenterally. The compounds are useful in the same manner as other similar agents and the dosage level is of the same order of magnitude as is generally employed in the treatment of psoriasis and related conditions.

A convenient form for administration of the present new compounds are salts of those compounds in which R$_3$ is OH, particularly salts with alkali metals such as sodium and potassium, the ammonium salt and salts with organic amines, particularly those commonly employed in pharmaceutical formulations. The salts, of course, should be pharmaceutically acceptable, that is the salt formation does not appreciably increase the toxicity of the therapeutic agents nor cause a toxic reaction in the host.

What is claimed is:
1. Compounds of the structure

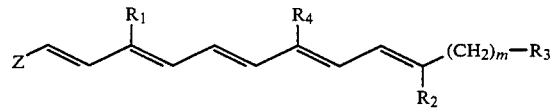

wherein
m is 0 to 1, and $R_1$ and $R_4$ are each independently hydrogen or an alkyl group of from 1 to 5 carbon atoms;

$R_2$ is an alkyl group of from 1 to 5 carbon atoms;

$R_3$ is $C_1$–$C_5$ alkoxy, phenyloxy, naphthyloxy, phenylalkoxy, naphthylalkoxy, retinoyloxy; and Z is a cyclohexyl, cyclohexenyl, or cyclohexadienyl group substituted with from 0 to 5 $C_1$–$C_5$ alkyl groups, an acetyl group or a hydroxyl group; and the pharmaceutically-acceptable salts thereof.

2. 1-Methoxy-2,5,9-trimethyl-11-(2,6,6-trimethyl-1-cyclohexen-1-yl)-2,4,6,8,10-undecapentaene.

3. 1-Retinyloxy-2,5,9-trimethyl-11-(2,6,6-trimethyl-1-cyclohexen-1-yl)-2,4,6,8,10-undecapentaene.

4. A pharmaceutical composition for the treatment of psoriasis and acne in a human host comprising, in combination with at least one pharmaceutically acceptable carrier, an effective amount of a compound of claim 1.

5. A method of treating psoriasis and acne in a human host which comprises administering to said host a therapeutically effective amount of at least one compound of claim 1.

* * * * *